(12) United States Patent
Murtagh et al.

(10) Patent No.: US 7,016,044 B2
(45) Date of Patent: Mar. 21, 2006

(54) OPTICAL MEASUREMENT APPARATUS AND METHOD

(75) Inventors: Martin Edward Murtagh, County Cork (IE); Patrick Vincent Kelly, County Galway (IE)

(73) Assignee: Optical Metrology Patents Limited, Cork (IE)

( * ) Notice: Subject to any disclaimer, the term of this patent is extended or adjusted under 35 U.S.C. 154(b) by 0 days.

(21) Appl. No.: 11/136,531

(22) Filed: May 25, 2005

(65) Prior Publication Data

US 2005/0213100 A1 Sep. 29, 2005

Related U.S. Application Data

(63) Continuation of application No. PCT/IE03/000157, filed on Nov. 27, 2003.

(60) Provisional application No. 60/429,312, filed on Nov. 27, 2002.

(30) Foreign Application Priority Data

Nov. 28, 2002 (IE) .................................. 2002/0914

(51) Int. Cl.
*G01N 21/00* (2006.01)

(52) U.S. Cl. ..................................................... 356/432

(58) Field of Classification Search ................ 356/432
See application file for complete search history.

(56) References Cited

U.S. PATENT DOCUMENTS

| 4,468,136 A | 8/1984 | Murphy et al. ................ 374/45 |
| 5,042,952 A | 8/1991 | Opsal et al. .................. 356/432 |
| 5,172,191 A | 12/1992 | Dutta et al. .................. 356/432 |
| 5,255,071 A | 10/1993 | Pollak et al. ................ 356/417 |

*Primary Examiner*—Gregory J. Toatley, Jr.
*Assistant Examiner*—Amanda Merlino
(74) *Attorney, Agent, or Firm*—Jacobson Holman PLLC

(57) ABSTRACT

A modulation spectroscopy system (1) directs a probe beam (11) onto a sample (10), the reflected probe beam being collected by a collector (7) and processed by a detector (8). A pump beam generated by a source (4, 5) directs a pump beam (13) onto the sample at the same spot as the probe beam. However, it also switches the pump beam via a path (14) onto an adjacent location not overlapping the probe spot. This is referred to as spatial modulation. A cylindrical lens (16) in the collection subsystem (7) collects reflected light including luminescence from both pump beam spots simultaneously, so that the luminescence becomes a d.c. signal which can be easily eliminated, including means from the modulator for varying pump beam intensities and positions. This provides means to reject the unwanted background luminescence signal as well as improvement to the signal to noise ratio.

17 Claims, 3 Drawing Sheets

OPTICAL MEASUREMENT APPARATUS AND METHOD

This is a continuation of PCT/IE03/000157 filed Nov. 27, 2003 and published in English which in turn is based on provisional Application No. 60/429,312 filed Nov. 27. 2002 and Irish Application No. 2002/0914 filed Nov. 28, 2002.

FIELD OF THE INVENTION

The invention relates to modulation spectroscopy.

PRIOR ART DISCUSSION

Modulation spectroscopy is a class of spectroscopy in which the reflectance (or transmission) of a material such as a semiconductor, an organic material, or a polymer is altered at some parts of the electromagnetic spectrum by means of an external perturbation. Generally, this perturbation is applied in a periodic manner, such that the reflectance of the semiconductor at the wavelengths where it changes in response to the external perturbation, periodically alternates between the value in the absence of external perturbation and that which it has in the presence of the external perturbation. In many methods of modulation spectroscopy, the perturbation is optically applied by means of a light beam. In such methods, the light beam used to perform the spectroscopy measurement is often referred to as the "probe" beam and the light beam which perturbs the reflectance of the material is generally referred to as the "pump" beam. The pump beam is generally coincident with the probe beam on the sample and is intensity modulated.

Modulated reflectance spectroscopy in which a periodically modulated pump light beam is directed on the material at the same point as the probe light beam used to perform reflectance spectroscopy is commonly referred to as photoreflectance spectroscopy.

U.S. Pat. No. 5,172,191 describes a method of photoreflectance spectroscopy in which the modulation of the reflectance of the sample material at the point of incidence of the probe light beam is performed. The pump beam is swept laterally in and out of coincidence with the probe beam at the sample.

U.S. Pat. No. 5,255,071 describes a method of photoreflectance spectroscopy in which the modulation of the pump beam is performed by acousto-optic modulation in which a single beam is amplitude modulated between "on" and "off" states in a single beam path.

A problem in conventional modulation reflectance spectroscopy is that the optical system for collecting the reflected probe beam also collects scattered luminescence which arises as a result of the pump beam incident on the same point of the sample as the probe beam. The pump beam will be more intense than the probe beam, which has been monochromated prior to its incidence on the sample, typically by at least an order of magnitude, and when the pump beam is switched off by a modulator, the luminescence will also be extinguished. A periodic luminescence signal, having the same frequency as the modulated reflectance signal is therefore also collected by the optical system for collecting the reflected probe beam. The luminescence signal from the pumped area of many samples, especially of certain types of semiconductor and light emitting polymer structures, can be more intense than the modulated reflectance signal. Furthermore, if no monochromator is present between the sample and the detector, the entire luminescence signal, at all emission wavelengths, enters the detector. As well as interfering with the main signal, background luminescence is also a major factor in the signal-to-noise ratio.

The invention addresses these problems.

SUMMARY OF THE INVENTION

According to the invention, there is provided a modulation spectroscopy method comprising the steps of directing a probe beam and a pump beam at a sample and modulating the pump beam, the probe beam being reflected from the sample, and the reflected probe beam being detected by a detector, wherein the pump beam is spatially modulated by moving its location of incidence on the sample between the probe beam location of incidence and a different location, and luminescence from both locations is received so that the luminescence is not modulated with the probe beam.

In one embodiment, the unmodulated luminescence and the modulated probe beam are detected by the same detector.

In another embodiment, the luminescence is received by a cylindrical lens whereby the axis of the cylindrical lens extends through both locations of incidence of the pump beam on the sample.

In a further embodiment, the output of the cylindrical lens is directed through a second cylindrical lens mounted perpendicularly to the first cylindrical lens.

In one embodiment, the method comprises the further steps of rejecting the received luminescence with a lock-in amplifier using a reference frequency derived from a drive signal for the pump beam modulator.

In another embodiment, the pump beam is spatially modulated by a modulator switching it between two discrete paths.

In a further embodiment, the modulator is an acousto-optic modulator driven with alternate drive frequency signals, each drive frequency providing first or higher order diffracted light on a different path, and the frequency of changing the drive frequency is the modulation (toggle) frequency.

In one embodiment, the modulator is controlled so that the pump beam intensity is varied to optimise reflectance and luminescence collection efficiency by the detector.

In another embodiment, the modulator is controlled so that it has a different intensity on each path to equalise luminescence from each location and thus to optimise modulated reflectance and d.c. luminescence collection efficiency by the detector.

In a further embodiment, the intensity is varied according to a feedback loop having a quadrant photodetector operating in a summation mode detecting pump beam intensity on the sample.

In one embodiment, the modulator is controlled so that the pump beam locations of incidence are changed to optimise reflectance and luminescence optical collection symmetry by the detector.

In another embodiment, the pump beam position is varied according to a feedback loop having a quadrant detector operating in a differential mode detecting positions of the pump beam on the sample.

In a further embodiment, the probe beam is monochromated before it is reflected from the sample.

In one embodiment, the method comprises the further step of separately detecting modulated luminescence from the location co-incident with the probe beam by a different means to that which detects the probe beam.

In another embodiment, the zeroth and any other diffraction orders other than the first order beam output from the modulator are terminated.

In a further embodiment, an interlock mechanism shuts power from the modulator (acousto-optic crystal) so that only the terminated zeroth order output exists.

According to another aspect, there is provided an optical measurement apparatus comprising means for performing a modulation spectroscopy method as defined above.

DETAILED DESCRIPTION OF THE INVENTION

Brief Description Of The Drawings

The invention will be more clearly understood from the following description of some embodiments of the apparatus thereof, given by way of example only with reference to the accompanying drawings in which.

DESCRIPTION OF THE EMBODIMENTS

Figure 1:
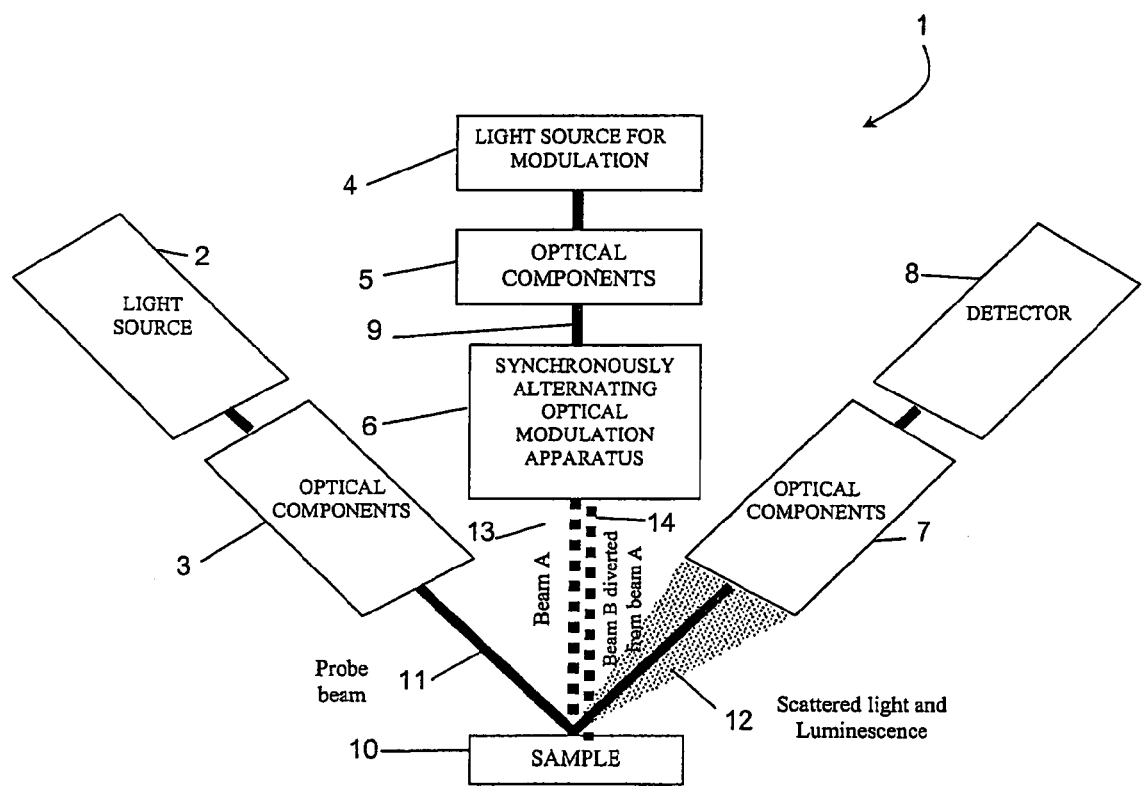
FIG. 1 shows a diagrammatic view of a modulation spectroscopy system of the invention.

Referring to FIG. 1, a modulation spectroscopy system comprises a probe light source 2 for producing a light beam having a broad spectrum of wavelengths, and beamsteering optical components 3 for shaping the light beam and coupling it to other components. Within the light source 2 a first monochromator disperses the wavelengths of light such that only a narrow range of wavelengths of the light are selected and transmitted. The beamsteering components 3 shape an input light beam to provide an output probe beam 11 coupled to a sample material 10.

A pump light source 4 produces a light beam having a single wavelength or a narrow spectrum of wavelengths, and beamsteering optical components 5 shaping it to provide a light beam 9. The wavelength of the pump light beam is chosen such that the corresponding photon energy is greater than that of the bandgap of a semiconductor material to be inspected, or is greater than the separation of two molecular electronic energy levels of a chemical substance to be inspected, or is otherwise sufficient in photon energy to cause the creation of photo-induced charge carrier in the material to be inspected. The pump beamsteering components 5 shape and steer the light beam.

A pump beam optical intensity modulator 6 modulates the intensity of the light steered to the point of incidence of the pump beam on the sample by means of alternating the position of incidence of the pump beam between a path 13 having a spot coincident with the probe beam spot and a separate discrete path 14 having a spot spaced-apart from the probe beam spot. This is referred to as spatial modulation. The modulator achieves this by having an acoustic-optical modulator device which diffracts the input light, the rf drive frequency of which is modulated between two frequency levels. At one drive frequency level the first order output light is at one deflection angle from the zeroth order straight-through axis, and at the other drive frequency level the first order deflection angle is different.

In general, the modulator operating parameters are as follows:

rf drive frequency of the acousto-optic modulator crystal, of the order of 100's MHz.

The frequency at which the beam is switched between the two discrete paths, namely the modulation or toggle frequency. This is typically in the range of hundreds of Hz to low MHz for modulation spectroscopy applications.

The angle between the two discrete paths (and thus the spatial separation on the sample) may be varied by varying one or both of the drive frequencies. Also, changing of both drive frequencies can be performed to achieve an equal shift of both beams with no mutual angle difference. Also, intensity of either or both beams may be varied by changing the amplitude of one or both of the drive frequencies. Furthermore, the duty cycle may be varied from 50:50 to any desired ratio by changing the modulation (toggling) duty cycle.

The use of a programmable controller for the acousto-optic modulator allows the intensity of the pump beam to be controlled at one or both locations with particular ease and versatility. A photosensitive detector positioned to detect all or part of the pump beam reflected from the sample can form part of a feedback device of an intensity control mechanism. Such an intensity control mechanism is used to vary the intensity of the modulated pump laser beam. The use of such a laser intensity feedback loop ensures the stability of the intensity of the laser spot in each of its two spatial positions of incidence on the sample. Beam spot position feedback is performed to vary the beam positions on the sample (by drive frequency control as set out above). In particular, the spot position may be detected by a position sensitive detector (PSD) of the type having a quadrant photodiode. A PSD may be used also for intensity detection for intensity feedback. For position detection the PSD is operated in a differential mode, and for intensity feedback it is operated in a summation mode.

There is a certain amount of straight-through zero order light, however, this is terminated. An interlock mechanism of the system shuts power from the modulator (acousto-optic crystal) as soon as a cover is opened or another safety-compromising event occurs. This causes the first order and any other higher diffraction order light to cease, leaving only the zero order light by default, which is safely terminated. This arrangement is fail-safe as the interlock mechanism is directly connected to the acousto-optic crystal, by-passing other circuits.

A detector beamsteering subsystem 7 comprises optical components for collecting and coupling the reflected probe light beam 11 reflected from a sample 10, as well as luminescence 12 from the sample 10. Importantly, the subsystem 7 comprises two mutually perpendicular cylindrical lenses, as described in more detail below. A detector 8 detects the reflected probe and luminescence.

A mechanical subsystem supports the various components so that with their optical axes are at equal angles relative to the sample such that the detector 8 detects the reflected probe and luminescence. An electronic subsystem records an electrical signal from the detector 8, and distinguishes periodic electrical signals of different frequencies from each other. A sample mounting subsystem holding the sample material may also comprise a means for moving the sample 10 relative to the light beams. A computer subsystem controls the several subsystems and processes recorded data. An electrical power subsystem provides mains and low voltage electrical power to the system.

The input probe beamsteering subsystem 3 and the output probe beamsteering subsystem 7 are mounted such that their optical axes make equal angles relative to the line normal to the surface of the sample 10. The sample 10 has a reflecting surface and is mounted such that the probe beam is reflected from the sample 10 into the optical path of the detector beamsteering subsystem 7. The pump beam components are mounted such that the pump beam, when not deflected or switched off by the modulator 6, is incident on the same position of the sample as the probe beam 11. For any angle of incidence of the probe beam on the sample which can be achieved using the mechanical assembly the pump beam at least fully covers the probe beam spot area on the sample 10. The pump beam components are mounted in most applications such that the angle of incidence of the pump beam is normal to the sample surface, however, this may be varied.

The sample 10 may be horizontally mounted, and the sample mounting subsystem may move the sample vertically up and down corresponding to the optimum alignment of the probe beam components.

The system's optical components may be mounted for optical coupling in free space or by fibre.

Figure 2:
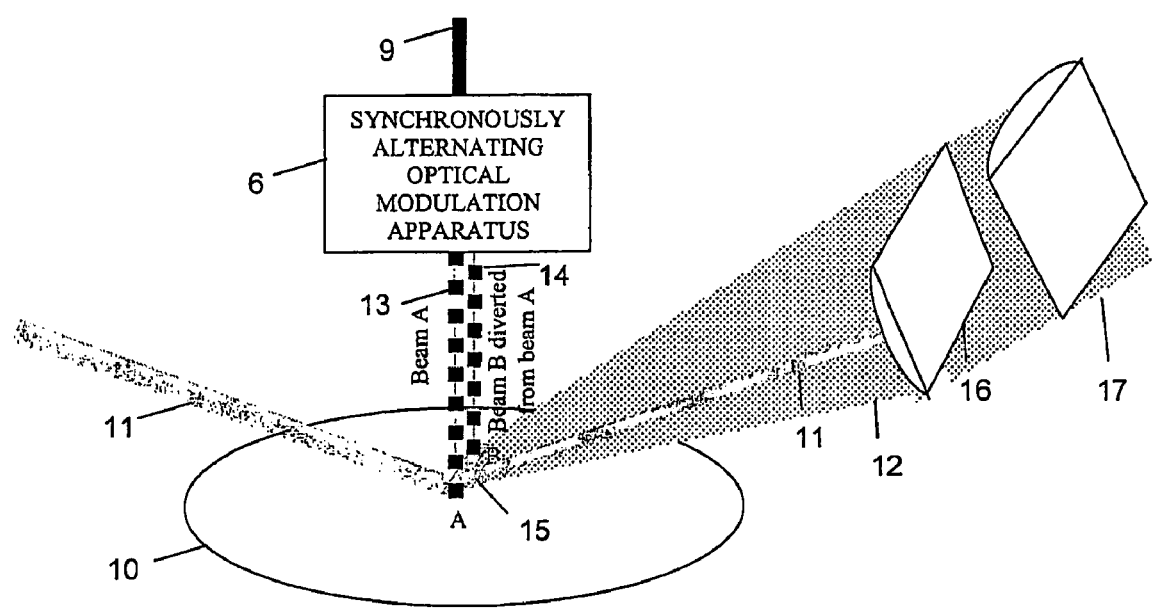
FIG. 2 is a diagram illustrating operation of the system of FIG. 1.

In operation, referring also to FIG. 2, the probe beam is directed to a sample, and its specular reflection from the sample "reflected probe beam" 11 is captured by lenses 16 and 17 and then recovered by detector 8. There is periodic illumination of the area of incidence of the probe beam on the sample by the pump beam at a modulation (toggle) frequency F, and with light of a photon energy which in the case of a semiconductor is greater than the bandgap energy of the semiconductor, and in the case of other sample materials which is of sufficient energy to photogenerate charge carriers in the material.

There is detection of the time-invariant reflected probe beam intensity (denoted R) and any amplitude modulated time-variant component of the reflected probe beam intensity (denoted $\Delta R$) at the modulation or toggle frequency F of the pump beam. The ratio $\Delta R/R$ is known at a number of different wavelengths of the probe beam. Scattered light (including luminescence) from the sample is collected in the detector.

The probe beam 11 may be delivered to the sample as a monochromatic beam, having a narrow range of wavelengths, in order to expose the sample to the minimum possible intensity of light in the condition in which the pump beam 13 is diverted from the point of incidence of the probe beam 11 on the sample.

The pump beam generates the luminescence signal, as well as the modulation of the reflectance signal. However in the system 1 it is spatially modulated so that it has two areas of incidence on the sample, both of which generate a luminescence signal of equal magnitude (providing that the sample has equal luminescence signal yield at two of these areas at least). The luminescence signals from each of said two areas have the same efficiency of collection and detection by the subsystem 7. One of the areas of incidence of the pump beam covers at least all of the area of incidence of the probe beam on the sample, and the other area of incidence of the pump beam covers none of the area of incidence of the probe beam on the sample. Modulation of the reflectance signal is achieved, not by the intensity modulation of the pump beam, for example by periodically chopping it or periodically switching it on and off, but by switching the pump beam periodically between the two discrete paths. The resultant signal collected by the output probe beam subsystem and detected by the detector 8 consists of an unchanging or d.c. luminescence signal, a d.c. reflectance signal, and an a.c. modulated reflectance signal. There exist many known methods of electronically separating the a.c. modulated reflectance signal from the d.c. signals, such that the modulated reflectance signal may be measured in the absence of a modulated luminescence interference.

As stated above and as illustrated in FIG. 2, the beamsteering subsystem 7 comprises two mutually perpendicular cylindrical lenses 16 and 17 which collect from the two areas of incidence of the pump beam on the sample into a beam of nearly circular cross-section, suitable for further imaging to the detector using spherical optics. This achieves reliably equal luminescence collection efficiency for each pump beam area of incidence, rendering the luminescence collected in this way as a d.c. signal. It is important to ensure in system set-up that the cylindrical lenses 16 and 17 are positioned so that their optical centre is aligned with the centroid between the two spot locations.

The invention therefore eliminates the undesirable collection of modulated luminescence signals in the modulated reflected probe beam path. The use of a synchronously alternating spatial modulation to produce a pump light beam on either of two discrete paths is advantageous. Further, the intensity on the paths can be separately or together varied for optimal collection of dc luminescence. The intensity control is achieved by changing the intensity of the drive signal for the relevant path. There is also the ability to vary the divergence or spacing of the two discrete paths. This is achieved changing one or both of the drive frequencies. Changing drive frequencies can also move both beams equally i.e. in tandem, to ensure symmetric optical collection. Also, use of a cylindrical lens has the effect of collecting the luminescence from the sample with equal efficiency from the area of incidence of both pump beams. Further, by providing a second cylindrical lens perpendicular to the first, collected light is fully collimated into a parallel beam for downstream processing.

Figure 3:
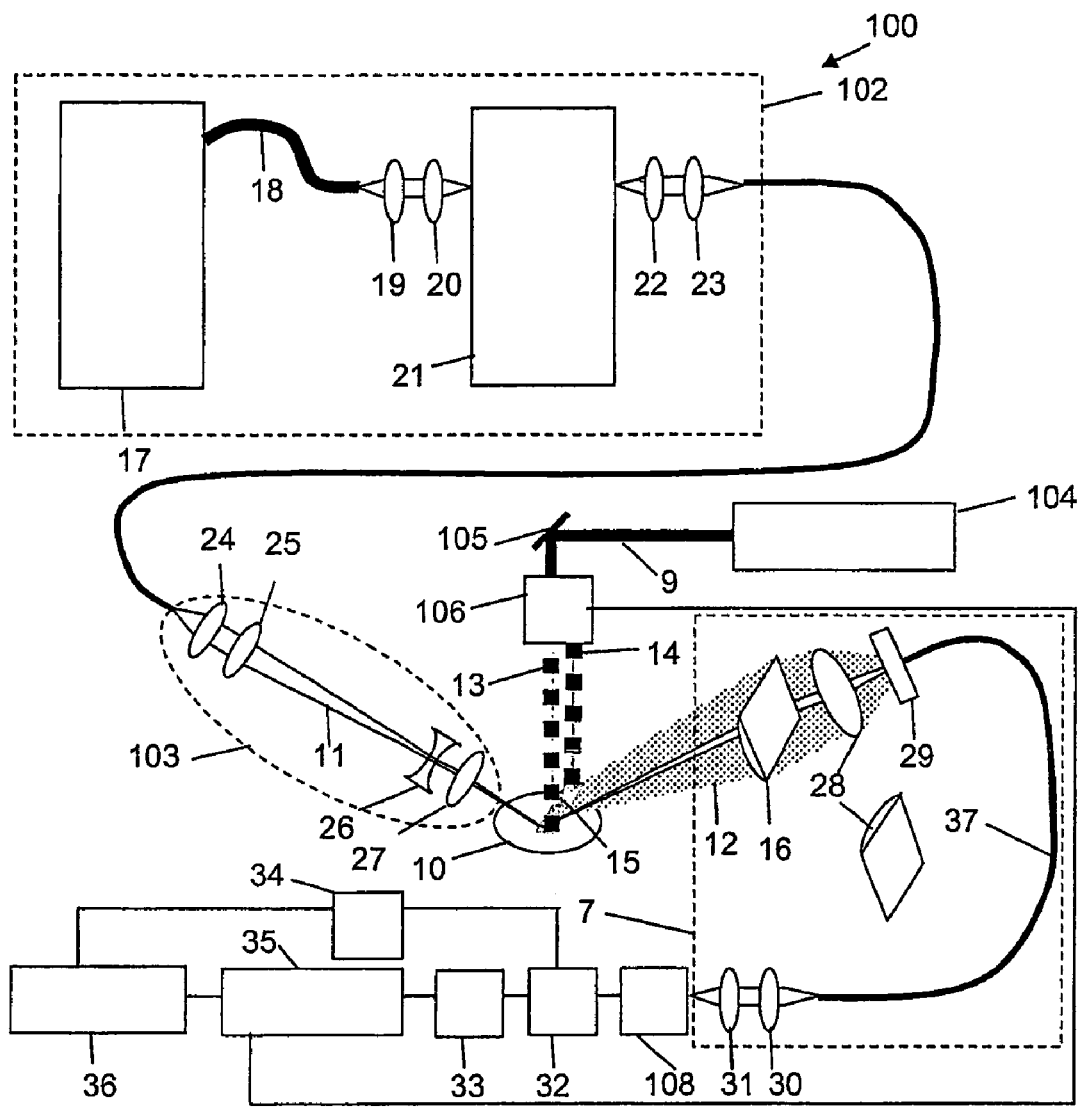
FIG. 3 is a diagrammatic view of another system of the invention.

Another system, 100, of the invention is illustrated in FIG. 3. A probe beam light source subsystem 102 comprises a light source 17 coupled by a fibre optic 18 and a pair of lenses 19 and 20. The lens 19 has a suitable f-number compared to the f-number of the fibre optic 18 and the other lens 20 has a suitable f-number compared to the f-number of a monochromator 21 such that it causes the light from lens 20 to fill most of the width of the grating of the monochromator 21 to obtain a near-optimum spectral resolution and throughput from the monochromator 21. This produces a monochromated light beam which is coupled by means of a pair of lenses 22 and 23 of suitable f-number into an input fibre for delivery to a probe input beamsteering subsystem 103. Regarding the term "f-number" above, this is well understood in the art, dealing with light gathering power or 'speed' of lens or collection optic. However, for avoidance of doubt it is the ratio of the focal length of the lens to the effective diameter of its aperture.

The input optical probe beamsteering subsystem 103 comprises a pair of lenses 24 and 25, the second of which is the objective lens of a Galilean telescope, an eyepiece lens 26 of which is placed such that a parallel probe beam 11 of de-magnified diameter is produced at the output of lens 26 and is focused using a high-f-number lens 27 onto a sample material 10.

A pump optical source 104 is coupled by a mirror 105 to a synchronously alternating spatial modulator 106, which modulates a pump beam 9 into a pair of spatially distinct, alternately modulated paths 13 and 14. The path 13 is directed to the area of incidence of the probe beam 11 on the sample 10, and the other path 14 is directed to an area of incidence on the sample 10 which is not overlapping the probe beam 11 spot.

An output optical probe beam subsystem comprises a cylindrical lens 16 oriented such that it has a line focus 15 overlapping both pump beam areas of incidence at the sample 10. A spherical lens 28 couples the beam through a filter 29 into a fibre optic 37. Instead of a spherical lens 28, the system may comprise a second cylindrical lens as shown in FIG. 2, thus providing a fully collimated output beam. The output of the fibre 37 is coupled through a pair of lenses 30 and 31 of suitable f-number onto a photo-sensitive detector 108, which is a silicon photodiode detector or an indium gallium arsenide photodiode detector.

The electrical signal produced by the detector 108 is coupled through a trans-impedance 32 and pre-amplifier 33 stage to a lock-in amplifier 35 which uses a reference frequency signal derived from the same source as that driving the modulator. The signals read by the lock-in amplifier are read by a controlling computer 36, which controls several of the other components of the system. The magnitude of the constant d.c. current or voltage from the detector 108 is also measured and recorded by the meter 34 whose output is read by the controlling computer 36. This constant d.c. current or voltage signal from the detector 108 is the unmodulated reflectance R of the sample at the transmission wavelength of the monochromator 21 with a very small additional constant luminescence signal. This is negligible by comparison with the size of the reflectance signal.

The result of the measurement is expressed as the dimensionless quantity $\Delta R/R$. The measurement of $\Delta R/R$ is repeated at a number of wavelengths by programmably adjusting the transmission wavelength of the monochromator 21, to acquire a spectrum of the modulated reflectance $\Delta R/R$ of the sample 10.

In another embodiment, one or more phase shifts may be introduced into the modulated reflected probe beam intensity component electrical signal from the photodetector, such that the signal may be measured under several different phase conditions and a phase analysis may be performed. The lock-in amplifier may contain the necessary electronic devices to perform this phase shifting, namely two-channel lock-in (simultaneous in-phase and quadrature phase analysis).

It will be appreciated that the cylindrical lens collects the luminescence from these areas (only one of which is luminescencing at any point in time) into a beam of nearly circular cross-section (due to the use of a pair of mutually perpendicular cylindrical lenses) suitable for further imaging to the detector. This arrangement, in combination with the synchronously alternating spatial modulation of the pump beams, reliably achieves an equal luminescence collection efficiency for each pump beam area of incidence, rendering the luminescence collected in this way as a d.c. signal. It will also be appreciated that the ability to separately or together dynamically vary the pump beam intensity and position with use of feedback allows dynamic maintenance of the luminescence as a d.c. signal.

Certain embodiments of the invention may additionally comprise one or more of the following additional subsystems.

A second, auxiliary, monochromator subsystem between the output probe beam subsystem and the detector subsystem and optically coupled by fibre to the these subsystems.

A fourth optical collection subsystem for luminescence and scattered light collection.

A third monochromator subsystem for luminescence and scattered light monochromation. This may incorporate an integrated detector or array of detectors such that the light entering the subsystem produces an electrical signal to simultaneously produce a measure of the spectral distribution of intensity in the lamp.

A second detector subsystem for pump beam detection. This may form part of the luminescence and scattered light monochromator subsystem.

Microscopic optical components forming part of the input probe beam subsystem for reducing the diameter of the incidence spot of the light steered to the sample to the minimum size possible having regard to the limitations introduced by diffraction effects and the aberrations inherent in practical lens systems.

A wafer manipulation subsystem for selecting a semiconductor wafer, which may have one of a range of diameters, from one or more cassettes or trays of such wafers, and placing the semiconductor wafer on the sample mounting subsystem such that a selected point on the wafer is at the point of incidence of the light beam from the input probe beam subsystem.

In some embodiments of the invention, the input probe beam subsystem and the principal monochromator subsystem may be replaced by an array of monochromatic light sources of different peak wavelengths, together with wavelength-selective optical filters in some embodiments, optical components for shaping one or more light beams from these sources. The detector system may include multiple lock-in amplifiers.

The invention finds application in the following technical fields, among others:

Measurement of the bandgap of semiconductor layers at room temperature.

Measurement of the alloy mole fraction in compound semiconductor layers and wafers.

Measurement of surface and interfacial electric fields in semiconductor layers and wafers.

Characterisation of electronic transitions and band structure in semiconductor layers and wafers.

Characterisation of semiconductor surfaces and interfaces.

Characterisation of chemical, ion, electron, or plasma induced damage or modification effects in semiconductor layers and wafers or at their surfaces and interfaces.

Characterisation of lattice mismatch in epitaxially grown semiconductor structures.

Characterisation of stress-induced strain effects in semiconductor layers and wafers.

Characterisation of quantum well semiconductor structures.

Characterisation of quantum dot semiconductor structures.

Characterisation of semiconductor heterostructures and related devices.

Characterisation of semiconductor laser and light-emitting structures and related devices.

Characterisation of organic and polymer light emitting devices and materials.

Characterisation of the active laser layer and etalon or reflecting cavity layers in a vertical cavity surface emitting laser or light emitting compound semiconductor structure whether on an epitaxial wafer or in a material sample or device, such that their modulation spectroscopy responses are distinguished by means of performing the modulated reflectance measurement at more than one angle of incidence.

Measurement of the base-collector and base-emitter internal electric fields in a heterojunction bipolar transistor epitaxial wafer, or other internal, interfacial or surface electric fields in a multilayer epitaxial structure. It may also be applied to corresponding base-emitter and base-collector light intensity analysis.

Any of the measurements or characterisation applications listed above when performed as a function of the application of an external stress to the sample, such as the heat applied during solder reflow or bonding or brasing of a semiconductor or other material of device to a second material or device.

It is envisaged that the spatial modulation may be achieved using a modulator other that that described. For example, a scanning mirror may be used. While this may not allow the same degree of dynamic control as an acousto-optic modulator crystal, it may be adequate in some applications as it achieves spatial modulation and the optical system collects from both locations simultaneously.

It will be appreciated that the invention improves upon the prior art in providing a method of significantly reducing periodically modulated luminescence interferences present in the photoreflectance light beam. The method improves upon sweeping photoreflectance techniques by the use of one of a pair of synchronously alternating and spatially separated light beams for modulation of the reflectance, such that both beams are incident on the sample of the material to be characterised at distinctly separate but closely spaced areas. The pump beam is present on one or other of two discrete beam paths, such that it can be rapidly switched between these paths, and the paths themselves can be varied in their mutual divergence and/or separation. The intensity of the beam can be caused to be the same when on either path, or can be chosen to be different on each path. The duty cycle of the beam on each path need not be 50%, but the beam can be caused to spend more time on one path than on the other, as desired. Suitable optical systems collect the luminescence interference from both areas of incidence of the beam pair as a continuous signal rather than a periodically alternating signal, such that frequency selective apparatus for periodic signal recovery which discriminates against very slowly varying quasi-constant or constant signals, can only detect the modulated reflectance signal, in the absence of significant periodically modulated luminescence. The invention affords a high signal to noise ratio in all applications of modulation spectroscopy, and is especially advantageous in the application of modulation spectroscopy to the characterisation of highly luminescent materials such as compound semiconductor and organic layers and structures made for photonic device fabrication. The invention represents a significant improvement over the prior art arrangements in which background luminescence is a major source of noise.

The invention is not limited to the embodiments described but may be varied in construction and detail.

The invention claimed is:

1. A modulation spectroscopy method comprising the steps of:
   directing a probe beam and a pump beam at a sample, the probe beam being reflected from the sample
   modulating the pump beam,
   a detector detecting the reflected probe beam,
   wherein the pump beam is spatially modulated by moving its location of incidence on the sample between the probe beam location of incidence and a different location, and
   luminescence from both locations is received so that the luminescence is not modulated with the probe beam.

2. A modulation spectroscopy method as claimed in claim 1, wherein the unmodulated luminescence and the modulated probe beam are detected by the same detector.

3. A modulation spectroscopy method as claimed in claims 1, wherein the luminescence is received by a cylindrical lens whereby the axis of the cylindrical lens extends through both locations of incidence of the pump beam on the sample.

4. A modulation spectroscopy method as claimed in claim 1, wherein the luminescence is received by a cylindrical lens whereby the axis of the cylindrical lens extends through both locations of incidence of the pump beam on the sample; and wherein the output of the cylindrical lens is directed through a second cylindrical lens mounted perpendicularly to the first cylindrical lens.

5. A modulation spectroscopy method as claimed in claim 1, comprising the further steps of rejecting the received luminescence with a lock-in amplifier using a reference frequency derived from a drive signal for a pump beam modulator.

6. A modulation spectroscopy method as claimed in claim 1, wherein the pump beam is spatially modulated by a modulator switching it between two discrete paths.

7. A modulation spectroscopy method as claimed in claim 6, wherein the modulator is an acousto-optic modulator driven with alternate drive frequency signals, each drive frequency providing first or higher order diffracted light on a different path, and the frequency of changing the drive frequency is the modulation frequency.

8. A modulation spectroscopy method as claimed in claim 6, wherein the modulator is controlled so that the pump beam intensity is varied to optimise reflectance and luminescence collection efficiency by the detector.

9. A modulation spectroscopy method as claimed in claim 6, wherein the modulator is controlled so that the pump beam intensity is varied to optimise reflectance and luminescence collection efficiency by the detector; and wherein the modulator is controlled so that it has a different intensity on each path to equalise luminescence from each location and thus to optimise modulated reflectance and d.c. luminescence collection efficiency by the detector.

10. A modulation spectroscopy method as claimed in claim 6, wherein the modulator is controlled so that the pump beam intensity is varied to optimise reflectance and luminescence collection efficiency by the detector; and wherein the intensity is varied according to a feedback loop having a quadrant photodetector operating in a summation mode detecting pump beam intensity on the sample.

11. A modulation spectroscopy method as claimed in claim 6, wherein the modulator is controlled so that the pump beam locations of incidence are changed to optimise reflectance and luminescence optical collection symmetry by the detector.

12. A modulation spectroscopy method as claimed in claim 11, wherein the pump beam position is varied according to a feedback loop having a quadrant detector operating in a differential mode detecting positions of the pump beam on the sample.

13. A modulation spectroscopy method as claimed in claim 1, wherein the probe beam is monochromated before it is reflected from the sample.

14. A modulation spectroscopy method as claimed in claim 1, comprising the further step of separately detecting modulated luminescence from the location co-incident with the probe beam by a different means to that which detects the probe beam.

15. A modulation spectroscopy method as claimed in claim 6, wherein the modulator is an acousto-optic modulator driven with alternate drive frequency signals, each drive frequency providing first or higher order diffracted light on a different path, and the frequency of changing the drive frequency is the modulation frequency; and wherein the zeroth and any other diffraction orders other than the first order beam output from the modulator are terminated.

16. A modulation spectroscopy method as claimed in claim 6, wherein the modulator is an acousto-optic modulator driven with alternate drive frequency signals, each drive frequency providing first or higher order diffracted light on a different path, and the frequency of changing the drive frequency is the modulation frequency; and wherein the zeroth and any other diffraction orders other than the first order beam output from the modulator are terminated; and wherein an interlock mechanism shuts power from the modulator so that only the terminated zeroth order output exists.

17. An optical measurement apparatus comprising means for performing a modulation spectroscopy method as claimed in claim 1.

* * * * *